United States Patent
Yuan et al.

(10) Patent No.: US 11,033,475 B2
(45) Date of Patent: *Jun. 15, 2021

(54) ORAL CARE COMPOSITIONS AND METHODS FOR WHITENING TEETH

(71) Applicant: Colgate-Palmolive Company, New York, NY (US)

(72) Inventors: Shaotang Yuan, East Brunswick, NJ (US); Guofeng Xu, Plainsboro, NJ (US); Jennifer Gronlund, Flemington, NJ (US); Robert Dicosimo, Chadds Ford, PA (US); Sharon Haynie, Philadelphia, PA (US); Mark Payne, Wilmington, DE (US)

(73) Assignee: Colgate-Palmolive Company, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/564,693

(22) Filed: Sep. 9, 2019

(65) Prior Publication Data

US 2019/0388326 A1  Dec. 26, 2019

Related U.S. Application Data

(63) Continuation of application No. 15/838,916, filed on Dec. 12, 2017, now Pat. No. 10,426,719.

(60) Provisional application No. 62/436,834, filed on Dec. 20, 2016.

(51) Int. Cl.

| A61K 8/66 | (2006.01) |
|---|---|
| A61K 8/22 | (2006.01) |
| A61K 8/37 | (2006.01) |
| A61K 8/81 | (2006.01) |
| A61K 8/90 | (2006.01) |
| A61Q 11/00 | (2006.01) |
| A61K 8/25 | (2006.01) |
| A61K 8/86 | (2006.01) |

(52) U.S. Cl.
CPC ............... *A61K 8/66* (2013.01); *A61K 8/22* (2013.01); *A61K 8/25* (2013.01); *A61K 8/37* (2013.01); *A61K 8/8176* (2013.01); *A61K 8/86* (2013.01); *A61K 8/90* (2013.01); *A61Q 11/00* (2013.01); *A61K 2800/31* (2013.01); *A61K 2800/48* (2013.01); *A61K 2800/52* (2013.01)

(58) Field of Classification Search
CPC ...... A61Q 11/00; A61K 2800/52; A61K 8/37; A61K 2800/31; A61K 2800/48; A61K 8/25; A61K 8/66; A61K 8/86; A61K 8/90; A61K 8/22; A61K 8/8176
See application file for complete search history.

(56) References Cited

U.S. PATENT DOCUMENTS

| 6,221,341 | B1 | 4/2001 | Montgomery | |
|---|---|---|---|---|
| 7,189,385 | B2 | 3/2007 | Montgomery | |
| 8,158,686 | B2 | 4/2012 | Bouillo et al. | |
| 8,389,254 | B2 | 3/2013 | Dicosimo et al. | |
| 8,540,971 | B2 | 9/2013 | Zaidel et al. | |
| 8,735,125 | B2* | 5/2014 | Dicosimo | C12N 9/18 435/197 |
| 8,932,563 | B2* | 1/2015 | Martinetti | A61P 39/06 424/49 |
| 9,884,000 | B2 | 2/2018 | Boyd et al. | |
| 9,974,634 | B2 | 5/2018 | Maloney et al. | |
| 10,098,824 | B2 | 10/2018 | Boyd et al. | |
| 10,413,500 | B2* | 9/2019 | Gronlund | A61K 8/66 |
| 10,426,719 | B2* | 10/2019 | Yuan | A61K 8/22 |
| 2005/0036956 | A1 | 2/2005 | Fei et al. | |
| 2006/0024246 | A1 | 2/2006 | Maitra et al. | |
| 2006/0045854 | A1 | 3/2006 | Zaidel et al. | |
| 2007/0071695 | A1 | 3/2007 | Chopra et al. | |
| 2007/0071696 | A1 | 3/2007 | Wang et al. | |
| 2012/0244091 | A1 | 9/2012 | Chopra et al. | |
| 2018/0168983 | A1* | 6/2018 | Pillai | A61K 8/442 |
| 2019/0388327 | A1* | 12/2019 | Gronlund | A61K 8/22 |

FOREIGN PATENT DOCUMENTS

| KR | 101197673 | 11/2012 |
|---|---|---|
| WO | 2012/087970 | 6/2012 |
| WO | 2013/148190 | 10/2013 |

OTHER PUBLICATIONS

International Search Report and Written Opinion of the International Searching Authority in International Application No. PCT/US2017/065744, dated Mar. 5, 2018.

* cited by examiner

*Primary Examiner* — Ganapathirama Raghu

(57) ABSTRACT

An oral care composition including an enzyme and an anhydrous matrix that at least partially stabilizes the enzyme. The anhydrous matrix includes a source of hydrogen peroxide, an acyl donor, a non-aqueous anhydrous liquid, and a thickener.

19 Claims, No Drawings

Specification includes a Sequence Listing.

SEQUENCE LISTING

<160> NUMBER OF SEQ ID NOS: 3

<210> SEQ ID NO 1
<211> LENGTH: 325
<212> TYPE: PRT
<213> ORGANISM: Thermotoga maritima

<400> SEQUENCE: 1

Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Glu Thr Leu
            20                  25                  30

Ala Glu Ser Glu Lys Phe Pro Leu Asp Pro Val Phe Glu Arg Met Glu
        35                  40                  45

Ser His Leu Lys Thr Val Glu Ala Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80

```
Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Gly Pro Val Asp Pro Gln Tyr Pro Gly Phe
    130                 135                 140

Met Thr Arg Gly Ile Leu Asp Pro Arg Thr Tyr Tyr Arg Arg Val
145                 150                 155                 160

Phe Thr Asp Ala Val Arg Ala Val Glu Ala Ala Ser Phe Pro Gln
                165                 170                 175

Val Asp Gln Glu Arg Ile Val Ile Ala Gly Ser Gln Gly Gly Gly
            180                 185                 190

Ile Ala Leu Ala Val Ser Ala Leu Ser Lys Lys Ala Lys Ala Leu Leu
        195                 200                 205

Cys Asp Val Pro Phe Leu Cys His Phe Arg Arg Ala Val Gln Leu Val
210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Ile Pro Ala Leu Phe Ser Val Gly Leu
            260                 265                 270

Met Asp Asn Ile Ser Pro Pro Ser Thr Val Phe Ala Ala Tyr Asn Tyr
        275                 280                 285

Tyr Ala Gly Pro Lys Glu Ile Arg Ile Tyr Pro Tyr Asn Asn His Glu
    290                 295                 300

Gly Gly Gly Ser Phe Gln Ala Val Glu Gln Val Lys Phe Leu Lys Lys
305                 310                 315                 320

Leu Phe Glu Lys Gly
                325

<210> SEQ ID NO 2
<211> LENGTH: 318
<212> TYPE: PRT
<213> ORGANISM: Bacillus subtilis

<400> SEQUENCE: 2

Met Gln Leu Phe Asp Leu Pro Leu Asp Gln Leu Gln Thr Tyr Lys Pro
1               5                   10                  15

Glu Lys Thr Ala Pro Lys Asp Phe Ser Glu Phe Trp Lys Leu Ser Leu
                20                  25                  30

Glu Glu Leu Ala Lys Val Gln Ala Glu Pro Asp Leu Gln Pro Val Asp
            35                  40                  45

Tyr Pro Ala Asp Gly Val Lys Val Tyr Arg Leu Thr Tyr Lys Ser Phe
    50                  55                  60

Gly Asn Ala Arg Ile Thr Gly Trp Tyr Ala Val Pro Asp Lys Gln Gly
65                  70                  75                  80

Pro His Pro Ala Ile Val Lys Tyr His Gly Tyr Asn Ala Ser Tyr Asp
                85                  90                  95

Gly Glu Ile His Glu Met Val Asn Trp Ala Leu His Gly Tyr Ala Ala
            100                 105                 110

Phe Gly Met Leu Val Arg Gly Gln Gln Ser Ser Glu Asp Thr Ser Ile
        115                 120                 125
```

```
Ser Leu His Gly His Ala Leu Gly Trp Met Thr Lys Gly Ile Leu Asp
    130                 135                 140

Lys Asp Thr Tyr Tyr Tyr Arg Gly Val Tyr Leu Asp Ala Val Arg Ala
145                 150                 155                 160

Leu Glu Val Ile Ser Ser Phe Asp Glu Val Asp Glu Thr Arg Ile Gly
                165                 170                 175

Val Thr Gly Gly Ser Gln Gly Gly Gly Leu Thr Ile Ala Ala Ala Ala
            180                 185                 190

Leu Ser Asp Ile Pro Lys Ala Ala Val Ala Asp Tyr Pro Tyr Leu Ser
        195                 200                 205

Asn Phe Glu Arg Ala Ile Asp Val Ala Leu Glu Gln Pro Tyr Leu Glu
    210                 215                 220

Ile Asn Ser Phe Phe Arg Arg Asn Gly Ser Pro Glu Thr Glu Val Gln
225                 230                 235                 240

Ala Met Lys Thr Leu Ser Tyr Phe Asp Ile Met Asn Leu Ala Asp Arg
                245                 250                 255

Val Lys Val Pro Val Leu Met Ser Ile Gly Leu Ile Asp Lys Val Thr
                260                 265                 270

Pro Pro Ser Thr Val Phe Ala Ala Tyr Asn His Leu Glu Thr Glu Lys
            275                 280                 285

Glu Leu Lys Val Tyr Arg Tyr Phe Gly His Glu Tyr Ile Pro Ala Phe
    290                 295                 300

Gln Thr Glu Lys Leu Ala Phe Phe Lys Gln His Leu Lys Gly
305                 310                 315

<210> SEQ ID NO 3
<211> LENGTH: 5
<212> TYPE: PRT
<213> ORGANISM: Artificial Sequence
<220> FEATURE:
<223> OTHER INFORMATION: Motif in CE-7 family
<220> FEATURE:
<221> NAME/KEY: misc_feature
<222> LOCATION: (2)..(2)
<223> OTHER INFORMATION: Xaa is any amino acid residue

<400> SEQUENCE: 3

Gly Xaa Ser Gln Gly
1               5
```

ORAL CARE COMPOSITIONS AND METHODS FOR WHITENING TEETH

CROSS REFERENCE TO RELATED APPLICATIONS

This application claims the benefit of U.S. patent application Ser. No. 15/838,916, filed on Dec. 12, 2017, and issued as U.S. Pat. No. 10,426,719, which claimed the benefit of U.S. provisional Patent Application Ser. No. 62/436,834, filed on Dec. 20, 2016, the disclosures of which are incorporated herein by reference in their entireties.

SEQUENCE LISTING

The instant application contains a Sequence Listing which has been submitted electronically in ASCII format and is hereby incorporated by reference in its entirety. Said ASCII copy, created on 13 Dec. 2016, is named 10858-00-OC_ST25.text and is 7000 bytes in size.

BACKGROUND

Conventional oral care products (e.g., toothpastes, whitening gels, etc.) and oral care whitening agents thereof are often utilized to whiten teeth. For example, conventional oral care whitening gels including hydrogen peroxide are often utilized to oxidize chromophores bound to surfaces of teeth to thereby whiten the teeth. While oral care whitening gels including hydrogen peroxide have proven to be effective for whitening teeth, different chromophores on the surfaces are often oxidized at varying rates and/or via varying mechanisms. Accordingly, oral care whitening gels including a single whitening agent (e.g., hydrogen peroxide) may require relatively longer periods of treatment to appreciably whiten the teeth.

In view of the foregoing, oral care products incorporating hydrogen peroxide often include an additional oral care whitening agent to facilitate the oxidation of the different chromophores to thereby shorten the periods of treatment. While the oral care products incorporating a variety of whitening agents have demonstrated increased efficacy in whitening teeth, there is a desire to utilize oral care whitening agents having relatively increased reactivity to thereby further reduce the periods of treatment. However, the oral care whitening agents having relatively increased reactivity are often unstable and subject to degradation. For example, the oral care whitening agents having relatively increased reactivity often react with other components of the oral care products and/or degrade, thereby reducing the effectiveness thereof.

What is needed, then, are improved oral care whitening compositions and methods for increasing the stability of the oral care whitening compositions.

BRIEF SUMMARY

This summary is intended merely to introduce a simplified summary of some aspects of one or more implementations of the present disclosure. Further areas of applicability of the present disclosure will become apparent from the detailed description provided hereinafter. This summary is not an extensive overview, nor is it intended to identify key or critical elements of the present teachings, nor to delineate the scope of the disclosure. Rather, its purpose is merely to present one or more concepts in simplified form as a prelude to the detailed description below.

The foregoing and/or other aspects and utilities embodied in the present disclosure may be achieved by providing an oral care composition including an enzyme having perhydrolytic activity and an anhydrous matrix configured to at least partially stabilize the enzyme having perhydrolytic activity. The anhydrous matrix may include a source of hydrogen peroxide, an acyl donor, a non-aqueous anhydrous liquid, and a thickener.

In at least one implementation, the enzyme has perhydrolytic activity and is capable of generating peracetic acid via enzyme-catalyzed perhydrolysis.

In another implementation, the source of hydrogen peroxide is a hydrogen peroxide complex, optionally, a cross-linked polyvinylpyrrolidone (PVP) hydrogen peroxide complex.

In another implementation, the oral care whitening complex is substantially free of water.

In another implementation, the acyl donor is selected from one or more of a $C_{2-18}$ carboxylic acid, a hydrolysable ester, and mixtures thereof.

In another implementation, the acyl donor is triacetin.

In another implementation, the thickener includes a cross-linked polyvinylpyrrolidone.

In another implementation, the thickener further includes a silica thickener.

In another implementation, the enzyme includes a CE-7 signature motif that aligns with SEQ ID NO: 2 using, e.g., CLUSTALW, the CE-7 signature motif including a) an RGQ motif at positions corresponding to positions 118-120 of SEQ ID NO: 2; b) a GXSQG (SEQ ID NO: 3) motif at positions corresponding to positions 179-183 of SEQ ID NO: 2 and an HE motif at positions corresponding to positions 298-299 of SEQ ID NO:2.

In another implementation, the enzyme includes an amino acid sequence including a CE-7 signature motif and having at least 80% amino acid sequence identity to SEQ ID NO:1.

In another implementation, the non-aqueous anhydrous liquid includes a polyethylene oxide-polypropylene oxide block copolymer.

In another implementation, the non-aqueous anhydrous liquid includes poly(ethylene glycol)-block-poly(propylene glycol)-block-poly(ethylene glycol).

In another implementation, the enzyme includes SEQ ID NO:1.

The foregoing and/or other aspects and utilities embodied in the present disclosure may also be achieved by providing a method for stabilizing the enzyme having perhydrolytic activity in the oral care composition of any of the preceding paragraphs. The method may include contacting the enzyme with the anhydrous matrix. The enzyme may be viable for at least 12 weeks at 40° C. and 75% relative humidity.

The foregoing and/or other aspects and utilities embodied in the present disclosure may also be achieved by providing a method for whitening teeth. The method may include contacting the oral care composition of any preceding paragraph with water on a surface of the teeth to generate peracetic acid.

Further areas of applicability of the present disclosure will become apparent from the detailed description provided hereinafter. It should be understood that the detailed description and specific examples, while indicating some typical aspects of the disclosure, are intended for purposes of illustration only and are not intended to limit the scope of the disclosure.

BRIEF DESCRIPTION OF BIOLOGICAL SEQUENCES

SEQ ID NO: 1 is the amino acid sequence of *Thermotoga maritima* C277S variant perhydrolase (also referred to herein as EZ-1).

SEQ ID NO: 2 is the amino acid sequence of a cephalosporin C deacetylase from *Bacillus subtilis* ATCC® 31954™.

SEQ ID NO: 3 is a motif, GXSQG, wherein X is any amino acid residue. This motif is shared among members of the carbohydrate esterase family 7 (CE-7 family).

DETAILED DESCRIPTION

The following description of various typical aspect(s) is merely exemplary in nature and is in no way intended to limit the disclosure, its application, or uses.

As used throughout, ranges are used as shorthand for describing each and every value that is within the range. Any value within the range may be selected as the terminus of the range. In addition, all references cited herein are hereby incorporated by reference in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

Additionally, all numerical values are "about" or "approximately" the indicated value, and take into account experimental error and variations that would be expected by a person having ordinary skill in the art. It should be appreciated that all numerical values and ranges disclosed herein are approximate values and ranges, whether "about" is used in conjunction therewith.

The present inventors have surprisingly and unexpectedly discovered that an anhydrous matrix provides increased stability for or stabilizes one or more enzymes having perhydrolytic activity (e.g., perhydrolase) of an oral care composition. Particularly, the anhydrous matrix is able to maintain the viability of the one or more enzymes having perhydrolytic activity for an extended period of time under accelerated aging conditions. The anhydrous matrix was also able to stabilize a source of hydrogen peroxide by maintaining or reducing the loss of hydrogen peroxide from the source of hydrogen peroxide in the presence of an acyl donor (e.g., triacetin) and the enzyme under accelerated aging conditions. The anhydrous matrix may include one or more sources of hydrogen peroxide, one or more acyl donors, one or more non-aqueous anhydrous liquids, a thickening system including one or more thickeners, and any combination or mixture thereof. The anhydrous matrix may be a base for any one or more oral care products (e.g., toothpaste, whitening gel, mouthwash, etc.) or oral care whitening compositions to thereby provide increased stability to the one or more enzymes having perhydrolytic activity in the oral care products or the oral care whitening compositions. In some implementations, the anhydrous matrix provides increased stability for the enzymes having perhydrolytic activity in the oral care products without encapsulations and/or film-type materials to enhance the stability thereof. The present inventors have also surprisingly and unexpectedly discovered that the anhydrous matrix maintains the stability of the enzyme in the oral care products and/or the anhydrous matrix thereof for at least 8 weeks, at least 12 weeks, at least 13 weeks, or greater, when exposed to accelerated aging conditions.

Oral Care Compositions

Compositions disclosed herein may be or include an oral care product or oral care composition and/or one or more components thereof. The oral care composition may be or include an oral care product (e.g., toothpaste, prophylactic paste, gel, etc.) including an oral care whitening composition. For example, the oral care composition may be or include a toothpaste including an oral care whitening composition. The oral care composition may also be or include an oral care whitening composition, and/or one or more components thereof. For example, the oral care composition may be or include an oral care whitening composition including an anhydrous matrix and one or more enzymes having perhydrolytic activity. In another example, the composition may be or include the anhydrous matrix of the oral care whitening composition. The anhydrous matrix may include one or more sources of hydrogen peroxide, one or more acyl donors, one or more non-aqueous anhydrous liquids, a thickening system including one or more thickeners, and any combination or mixture thereof. For example, the anhydrous matrix may include a thickening system including a thickener (e.g., a cross-linked polyvinylpyrrolidone) and a non-aqueous anhydrous liquid (e.g., a block co-polymer, such as Poly(ethylene glycol)-block-poly(propylene glycol)-block-poly(ethylene glycol)). In another example, the anhydrous matrix may include a source of hydrogen peroxide (e.g., a hydrogen peroxide complex), a thickener, and a non-aqueous anhydrous liquid. In at least one implementation, the anhydrous matrix may include a source of hydrogen peroxide and a non-aqueous anhydrous liquid, and the source of hydrogen peroxide (e.g., a hydrogen peroxide complex) may at least partially provide a thickener for the anhydrous matrix. As further described herein, the one or more enzymes having perhydrolytic activity may catalyze a reaction between the one or more sources of hydrogen peroxide, or the hydrogen peroxide generated therefrom, and the one or more acyl donors to generate an oral care whitening enhancer (e.g., peracetic acid).

The anhydrous matrix and the enzymes having perhydrolytic activity may be maintained together with one another in an oral care product or the oral care whitening composition thereof. For example, the enzymes having perhydrolytic activity may be contacted, mixed, commingled, agglomerated, or otherwise combined with the anhydrous matrix, which may include the sources of hydrogen peroxide, the acyl donors, the non-aqueous anhydrous liquids, and/or the thickening system including one or more thickeners. The anhydrous matrix and the enzymes of the oral care whitening composition may be mixed or maintained with one another in a single homogenous phase. In at least one implementation, the anhydrous matrix and the enzymes having perhydrolytic activity of the oral care whitening composition may be combined with one another in an anhydrous formulation or anhydrous composition. In at least one implementation, the enzyme may be stable or exhibit increased stability when contacted, mixed, or otherwise combined with the anhydrous matrix of the oral care whitening composition.

As used herein, "stability," "increased stability," and/or "high stability" may refer to an oral care whitening composition where the amount or concentration of the source of hydrogen peroxide or the hydrogen peroxide thereof is not reduced by more than 15%, more than 18%, more than 20%, more than 25%, or more than 30% over a period of at least 8 weeks, at least 10 weeks, at least 12 weeks, at least 13 weeks, or greater, when aged at a temperature of at least 40° C. and/or at about 75% relative humidity (RH). For example, a stable oral care whitening composition or an oral care whitening composition having "stability," "increased stability," and/or "high stability" may refer to an oral care whitening composition including the anhydrous matrix and the enzymes, typically in a single phase, where the amount of hydrogen peroxide in the source of hydrogen peroxide of the anhydrous matrix is not reduced by more than 15%, more than 18%, more than 20%, more than 25%, or more than 30% over a period of at least 8 weeks, at least 10 weeks, at least 12 weeks, at least 13 weeks, or greater, when aged at a temperature of at least 40° C. and 75% RH.

In at least one implementation, the oral care composition, including the gel matrix and the enzyme, prior to use may be anhydrous. For example, the oral care whitening composition may be free or substantially free of water. As used herein, "free" or "substantially free" may refer to a composition that contains less than 10.0 wt %, less than 5.0 wt %, less than 3.0 wt %, less than 1.0 wt %, less than 0.1 wt %, less than 0.05 wt %, less than 0.01 wt %, less than 0.005 wt %, or less than 0.0001 wt % based on a total weight of the oral care whitening composition. In at least one implementation, contacting at least a portion of the oral care whitening composition with water may initiate the release of hydrogen peroxide. For example, contacting the one or more sources of hydrogen peroxide of the anhydrous matrix with water initiates the release of hydrogen peroxide. In yet another example, contacting at least a portion of the oral care whitening composition with water initiates the generation of the whitening enhancer (e.g., peracetic acid).

Encapsulation and Film Type Polymers

In at least one implementation, the oral care composition does not include any encapsulations and/or film-type materials to enhance the stability thereof. For example, the oral care whitening composition does not include any water-soluble or water-insoluble encapsulations and/or film-type materials configured to separate (e.g., physically) any one or more of the sources of hydrogen peroxide, the acyl donors, the non-aqueous anhydrous liquids, and/or the thickening system from one another to thereby increase the stability of the oral care whitening composition. In another example, the oral care whitening composition does not include any polymeric encapsulations and/or film-type materials configured to separate (e.g., physically) any one or more of the sources of hydrogen peroxide, the acyl donors, the non-aqueous anhydrous liquids, and/or the thickening system from one another to thereby increase the stability of the oral care whitening composition. Illustrative encapsulations may be or include, but are not limited to, nano-capsules or shells, micro-capsules or shells, macro-capsules or shells, micro-emulsions, nano-emulsions, or the like or combinations thereof.

Sources of Hydrogen Peroxide

The oral care composition may include one or more sources of hydrogen peroxide. The one or more sources of hydrogen peroxide may be any compound or material configured to react with any one or more of the acyl donors and/or any one or more of the enzymes having perhydrolytic activity to form the oral care whitening enhancer. For example, the one or more sources of hydrogen peroxide may be or include any compound configured to provide or release hydrogen peroxide to react with the acyl donor and/or the enzymes having perhydrolytic activity to form the oral care whitening enhancer (e.g., peracetic acid). As previously discussed, the sources of hydrogen peroxide may be configured to release hydrogen peroxide when contacted with water. Illustrative sources of hydrogen peroxide may be or include, but are not limited to, hydrogen peroxide, urea peroxide, calcium peroxide, a cross-linked polyvinylpyrrolidone (PVP) hydrogen peroxide complex, a polyvinylpyrrolidone (PVP) hydrogen peroxide complex, sodium percarbonate, and the like, and combinations thereof. The sources of hydrogen peroxide may also be or include, but are not limited to, PEROXYDONE™ XL 10, which is commercially available from Ashland Inc. of Covington, Ky. In a typical implementation, the source of hydrogen peroxide includes a PVP peroxide complex.

In at least one implementation, the one or more sources of hydrogen peroxide may be or include one or more peroxide complexes. The peroxide complex may include a peroxide component and a porous cross-linked polymer. As used herein, a "peroxide component" may be or include any oxidizing compound including a bivalent oxygen-oxygen group. Peroxide components may be or include, but are not limited to, peroxides and hydroperoxides, such as hydrogen peroxide, peroxides of alkali and alkaline earth metals, organic peroxy compounds, peroxy acids, pharmaceutically-acceptable salts thereof, and the like, and combinations or mixtures thereof. Peroxides of alkali and alkaline earth metals may include, but are not limited to, lithium peroxide, potassium peroxide, sodium peroxide, magnesium peroxide, calcium peroxide, barium peroxide, and the like, and combinations or mixtures thereof. Organic peroxy compounds may include, but are not limited to, carbamide peroxide (e.g., urea hydrogen peroxide), glyceryl hydrogen peroxide, alkyl hydrogen peroxides, dialkyl peroxides, alkyl peroxy acids, peroxy esters, diacyl peroxides, benzoyl peroxide, monoperoxyphthalate, and the like, and combinations and mixtures thereof. Peroxy acids and their salts may include, but are not limited to, organic peroxy acids, such as alkyl peroxy acids, monoperoxyphthalate, and the like, and combinations or mixtures thereof. Peroxy acids and their salts may also be or include, but are not limited to, inorganic peroxy acid salts, such as percarbonate and perborate salts of alkali and alkaline earth metals (e.g., lithium, potassium, sodium, magnesium, calcium and barium), and the like, and combinations or mixtures thereof. In various implementations, the peroxide component includes hydrogen peroxide, urea peroxide, sodium percarbonate, and combinations or mixtures thereof. In another implementation, the peroxide component includes hydrogen peroxide.

In at least one implementation, the porous cross-linked polymer of the peroxide complex may be or include, but is not limited to, an N-vinyl heterocyclic polymer. The porous cross-linked polymer may be configured to adsorb, complex with, or otherwise retain the peroxide component. The porous cross-linked polymer may be configured to retain the peroxide component until release is initiated. For example, the porous cross-linked polymer may retain the peroxide component until contacted with water. In at least one implementation, the peroxide complex may be a particulate, such as a polymer particulate. The porous cross-linked polymer of the peroxide complex may control the release of the peroxide component from the peroxide complex. For example, the porous cross-linked polymer may hinder control (e.g., hasten or slow) the release of the peroxide component from the polymer particulate.

In at least one implementation, the N-vinyl heterocyclic polymer may be derived from a N-heterocyclic vinyl monomer, typically including N-vinyl heterocyclic monomers having from about 3 to about 7 atoms in a heterocyclic ring, including a carbonyl carbon atom and a nitrogen heteroatom containing a vinyl group. In a typical implementation, the ring contains five or six atoms including heteroatoms such as sulfur or oxygen, and may be substituted or unsubstituted.

In at least one implementation, the porous cross-linked polymer may be or include, but is not limited to, KOLLIDONE® and/or LUVICROSS®, both of which are commercially available from BASF of Mount Olive, N.J., PVP K-Series and/or POVIDONE™ K-30, which are commercially available from AAA International Corp. of Downers Grove, Ill., PVP K-30 USP24, PVP VA-64, PVP K-17, and PVP K-90, which are commercially available from Peakchem, Hangzhou, China, and POLYPLASDONE® INF-10, which is commercially available from ISP Corporation of Wayne, N.J.

The amount or concentration of the peroxide component present in the peroxide complex may vary widely. In at least one implementation, the amount of the peroxide component present in the peroxide complex may be from about 0.1 wt % to about 40 wt % based on a total weight of the peroxide complex. For example, the amount of the peroxide component present in the peroxide complex may be about 1 wt % to about 30 wt %, about 5 wt % to about 20 wt %, about 8 wt % to about 15 wt %, or about 10 wt % to about 13 wt %, based on a total weight of the peroxide complex. In a typical implementation, the source of the hydrogen peroxide includes a complex of hydrogen peroxide adsorbed into a cross-linked polyvinylpyrrolidone (PVP). For example, the source of the hydrogen peroxide includes PEROXYDONE™ XL 10 and/or PEROXYDONE™ K-30, both of which are commercially available from Ashland Inc. of Covington, Ky. In a typical implementation, the source of hydrogen peroxide is PEROXYDONE™ XL 10.

The amount or concentration of the source of hydrogen peroxide may vary widely. In at least one implementation, the amount of the source of hydrogen peroxide may be greater than or equal to 0.5 wt % and less than or equal to 10.5 wt % based on a total weight of the oral care whitening composition. For example, the amount of the source of hydrogen peroxide in the oral care whitening composition may be from about 0.5 wt %, about 1.0 wt %, about 1.5 wt %, about 2.0 wt %, about 2.5 wt %, about 2.0 wt %, about 2.5 wt %, about 3.0 wt %, about 3.5 wt %, about 4.0 wt %, about 4.5 wt %, or about 5.0 wt % to about 5.5 wt %, about 6.0 wt %, about 6.5 wt %, about 7.0 wt %, about 7.5 wt %, about 8.0 wt %, about 8.5 wt %, about 9.0 wt %, about 9.5 wt %, about 10.0 wt %, or about 10.5 wt %. In another example, the amount of the source of hydrogen peroxide in the oral care whitening composition may be from about 0.5 wt % to about 10.5 wt %, about 1.0 wt % to about 10.0 wt %, about 1.5 wt % to about 9.5 wt %, about 2.0 wt % to about 9.0 wt %, about 2.5 wt % to about 8.5 wt %, about 2.0 wt % to about 8.0 wt %, about 2.5 wt % to about 7.5 wt %, about 3.0 wt % to about 7.0 wt %, about 3.5 wt % to about 6.5 wt %, about 4.0 wt % to about 6.0 wt %, about 4.5 wt % to about 5.5 wt %, or about 5.0 wt % to about 6.0 wt %. In yet another example, the amount of the source of hydrogen peroxide in the oral care whitening composition may be less than or equal to 0.5 wt %, less than or equal to 1.0 wt %, less than or equal to 1.5 wt %, less than or equal to 2.0 wt %, less than or equal to 2.5 wt %, less than or equal to 2.0 wt %, less than or equal to 2.5 wt %, less than or equal to 3.0 wt %, less than or equal to 3.5 wt %, less than or equal to 4.0 wt %, less than or equal to 4.5 wt %, less than or equal to 5.0 wt %, less than or equal to 5.5 wt %, less than or equal to 6.0 wt %, less than or equal to 6.5 wt %, less than or equal to 7.0 wt %, less than or equal to 7.5 wt %, less than or equal to 8.0 wt %, less than or equal to 8.5 wt %, less than or equal to 9.0 wt %, less than or equal to 9.5 wt %, less than or equal to 10.0 wt %, or less than or equal to 10.5 wt %. In a typical implementation, the amount of the source of hydrogen peroxide in the oral care whitening composition may be about 5.5 wt %.

In another implementation, the amount of the source of hydrogen peroxide may be greater than or equal to 0.1 wt % and less than or equal to 2.0 wt % based on a total weight of the oral care whitening composition. For example, the amount of the source of hydrogen peroxide in the oral care whitening composition may be from about 0.1 wt %, about 0.2 wt %, about 0.3 wt %, about 0.4 wt %, about 0.5 wt %, about 0.6 wt %, about 0.7 wt %, about 0.8 wt %, about 0.9 wt %, or about 1.0 wt % to about 1.1 wt %, about 1.2 wt %, about 1.3 wt %, about 1.4 wt %, about 1.5 wt %, about 1.6 wt %, about 1.7 wt %, about 1.8 wt %, about 1.9 wt %, or about 2.0 wt %. In another example, the amount of the source of hydrogen peroxide in the oral care whitening composition may be from about 0.1 wt % to about 2.0 wt %, about 0.2 wt % to about 1.9 wt %, about 0.3 wt % to about 1.8 wt %, about 0.4 wt % to about 1.7 wt %, about 0.5 wt % to about 1.6 wt %, about 0.6 wt % to about 1.5 wt %, about 0.7 wt % to about 1.4 wt %, about 0.8 wt % to about 1.3 wt %, about 0.9 wt % to about 1.2 wt %, or about 1.0 wt % to about 1.1 wt %. In yet another example, the amount of the source of hydrogen peroxide in the oral care whitening composition may be less than or equal to 0.3 wt %, less than or equal to 0.4 wt %, less than or equal to 0.5 wt %, less than or equal to 0.6 wt %, less than or equal to 0.7 wt %, less than or equal to 0.8 wt %, less than or equal to 0.9 wt %, less than or equal to 1.0 wt %, less than or equal to 1.1 wt %, less than or equal to 1.2 wt %, less than or equal to 1.3 wt %, less than or equal to 1.4 wt %, less than or equal to 1.5 wt %, less than or equal to 1.6 wt %, less than or equal to 1.7 wt %, less than or equal to 1.8 wt %, less than or equal to 1.9 wt %, or less than or equal to 2.0 wt %.

Acyl Donor

The oral care composition may include one or more acyl donors. The one or more acyl donors may be or include any compound or material configured to react with any one or more of the sources of hydrogen peroxide, or the hydrogen peroxide thereof, and/or any one or more of the enzymes having perhydrolytic activity to form the oral care whitening enhancer. The acyl donors may be or include, but are not limited to, $C_{2-18}$ carboxylic acids, including lower linear or branched alkyl carboxylic acids, hydrolysable esters of $C_{2-18}$ carboxylic acids, and the like, and mixtures or combinations thereof. In at least one example, the $C_{2-18}$ carboxylic acids may be unsubstituted. In another example, the $C_{2-18}$ carboxylic acids may be substituted with a hydroxyl and/or a $C_{1-4}$ alkoxy group.

In at least one implementation, one or more of the acyl donors may be an ester represented by formula (1), $$[X]_m R_5 \qquad (1)$$

$$R_6 C(O)O \qquad (2)$$

where X is an ester group represented by the formula (2), $R_5$ is a $C_{1-6}$ linear, branched, or cyclic hydrocarbyl moiety, a five-member cyclic heteroaromatic moiety, or a six-member cyclic aromatic or heteroaromatic moiety, optionally substituted with hydroxyl groups, where each individually carbon atom in $R_5$ includes no more than one hydroxyl group, no more than one ester group, no more than one ester group or carboxylic acid group, where $R_5$ optionally includes one or more ether linkages, where m is an integer from 1 to the number of carbon atoms in $R_5$, and where the esters have a solubility in water of at least 5 ppm at 25° C.; where $R_6$ is a $C_1$ to $C_7$ linear, branched or cyclic hydrocarbyl moiety, optionally substituted with a hydroxyl group or $C_1$ to $C_4$ alkoxy group, wherein $R_6$ optionally includes one or more ether linkages where $R_6$ is $C_2$ to $C_7$.

In another implementation, one or more of the acyl donors may be a glyceride represented by the formula (3),

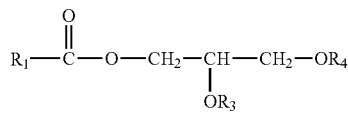 (3)

where $R_1$ is a $C_{1-7}$ straight or branch chain alkyl, optionally substituted with a hydroxyl or a $C_{1-4}$ alkoxy group, and $R_3$ and $R_4$ are individually an H or an $R_1C(O)$.

In another implementation, one or more of the acyl donors may be an ester represented by the formula (4),

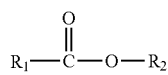 (4)

where $R_1$ is a $C_{1-7}$ straight or branch chain alkyl, optionally substituted with a hydroxyl or a $C_{1-4}$ alkoxy group, $R_2$ is a $C_{1-10}$ straight or branch chain alkyl, alkenyl, alkynyl, aryl, alkylaryl, alkylheteroaryl, heteroaryl, $(CH_2CH_2O)_n$, or $(CH_2CH(CH_3)-O)_nH$, and n is an integer from 1 to 10.

In yet another implementation, one or more of the acyl donors may be an acetylated saccharide. Illustrated acetylated saccharides may be or include, but is not limited to, acetylated monosaccharides, acetylated disaccharides, acetylated polysaccharide, and the like, and combinations thereof.

In at least one implementation, one or more of the acyl donors may be or include, but is not limited to, $C_{2-18}$ carboxylic acids, $C_{2-6}$ carboxylic acids (e.g., acetic acid), including lower linear or branched alkyl carboxylic acids, optionally substituted with hydroxy and/or $C_{1-4}$ alkoxy groups, hydrolysable and acceptable esters thereof (e.g., mono-, di-, and tri-glycerides, and acylated saccharides), and mixtures thereof. In at least one example, the acyl donors may be or include, but are not limited to 1,2,3-triacetoxypropane or triacetin or glycerin triacetate, acylated saccharides, and the like, and combinations thereof. In at least one implementation, the acyl donor or ester may have a water solubility of at least 5 ppm at 25° C. In a typical implementation, the acyl donor is 1,2,3-triacetoxypropane or triacetin (TA).

In at least one implementation, the acyl donors may be or include, but are not limited to, one or more acylated saccharides selected from acylated mono-, di-, and polysaccharides. In another implementation, the acylated saccharides are selected from acetylated xylan, fragments of acetylated xylan, acetylated xylose (e.g., xylose tetraacetate), acetylated glucose (e.g., α-D-glucose pentaacetate, β-D-glucose pentaacetate, 1-thio-β-D-glucose-2,3,4,6-tetraacetate), β-D-galactose pentaacetate, sorbitol hexaacetate, sucrose octaacetate, β-D-ribofuranose-1,2,3,5-tetraacetate, β-D-ribofuranose-1,2,3,4-tetraacetate, tri-O-acetyl-D-galactal, tri-O-acetyl-D-glucal, β-D-xylofuranose tetraacetate, β-D-glucopyranose pentaacetate, β-D-glucopyranose-1,2,3,4-tetraacetate, β-D-glucopyranose-2,3,4,6-tetraacetate, 2-acetamido-2-deoxy-1,3,4,6-tetracetyl-β-D-glucopyranose, 2-acetamido-2-deoxy-3,4,6-triacetyl-1-chloride-α-D-glucopyranose, β-D-mannopyranose pentaacetate, and acetylated cellulose. In a typical implementation, the acetylated saccharide is selected from β-D-ribofuranose-1,2,3,5-tetraacetate, tri-O-acetyl-D-galactal, tri-O-acetyl-D-glucal, sucrose octaacetate, and acetylated cellulose. In another implementation, the acyl donors may include 5-acetoxymethyl-2-furaldehyde, 3,4-diacetoxy-1-butene, 4-acetoxybenezoic acid, vanillin acetate, propylene glycol methyl ether acetate, methyl lactate, ethyl lactate, methyl glycolate, ethyl glycolate, methyl methoxyacetate, ethyl methoxyacetate, methyl 3-hydroxybutyrate, ethyl 3-hydroxybutyrate, and triethyl 2-acetyl citrate.

In yet another implementation, the acyl donors are selected from monoacetin, diacetin, triacetin, monopropionin, dipropionin, tripropionin, monobutyrin, dibutyrin, tributyrin, glucose pentaacetate, xylose tetraacetate, acetylated xylan, acetylated xylan fragments, β-D-ribofuranose-1,2,3,5-tetraacetate, tri-O-acetyl-D-galactal, tri-O-acetyl-D-glucal, monoesters or diesters of 1,2-ethanediol, 1,2-propanediol, 1,3-propanediol, 1,2-butanediol, 1,3-butanediol, 2,3-butanediol, 1,4-butanediol, 1,2-pentanediol, 2,5-pentanediol, 1,5-pentanediol, 1,6-pentanediol, 1,2-hexanediol, 2,5-hexanediol, 1,6-hexanediol, and mixtures thereof. In a further implementation, the acyl donor is propylene glycol diacetate (PGDA), ethylene glycol diacetate (EGDA), or a mixture thereof. In yet another implementation, the acyl donors are selected from monoacetin, diacetin, triacetin, monopropionin, dipropionin, tripropionin, monobutyrin, dibutyrin, and tributyrin. In yet another aspect, the acyl donor is selected from diacetin and triacetin.

The amount or concentration of the acyl donor may vary widely. In at least one implementation, the amount of the acyl donor may be at least partially determined by a target or desired concentration of peroxyacid or peracetic acid to be generated via enzyme-catalyzed perhydrolysis. For example, the target or desired concentration of peroxyacid or peracetic acid to be generated via enzyme-catalyzed perhydrolysis may be less than or equal to about 2,000 ppm, and the amount of the acyl donor present in the oral care whitening composition may be greater than or equal to 0.05 wt % and less than or equal to 40 wt % based on a total weight of the oral care whitening composition. For example, the amount of the acyl donor present in the oral care whitening composition may be from about 0.05 wt %, about 5 wt %, about 10 wt %, about 15 wt %, about 20 wt %, or about 25 wt % to about 30 wt %, about 35 wt %, or about 40 wt %. In another implementation, the amount of the acyl donor present in the oral care whitening composition may be less than 2 wt %. For example, the amount of the acyl donor present in the oral care whitening composition may be less than 10 wt %, less than 9.5 wt %, less than 9.0 wt %, less than 8.5 wt %, less than 8.0 wt %, less than 7.5 wt %, less than 7.0 wt %, less than 6.5 wt %, less than 6.0 wt %, less than 5.5 wt %, less than 5.0 wt %, less than 4.5 wt %, less than 4.0 wt %, less than 3.5 wt %, less than 3.0 wt %, less than 2.5 wt %, less than 2.0 wt %, less than 1.5 wt %, less than 1.0 wt %, less than 0.9 wt %, less than 0.8 wt %, less than 0.7 wt %, less than 0.6 wt %, less than 0.5 wt %, less than 0.4 wt %, less than 0.3 wt %, less than 0.2 wt %, or less than 0.1 wt %.

In at least one implementation, the amount of the acyl donor present in the oral care whitening composition may be from about 2 wt % to about 20 wt % based on a total weight of the oral care whitening composition. For example, the amount of the acyl donor present in the oral care whitening composition may be from about 10 wt %, about 11 wt %, about 12 wt %, about 13 wt %, or about 14 wt % to about 16 wt %, about 17 wt %, about 18 wt %, about 19 wt %, or about 20 wt %. In another example, the amount of the acyl donor present in the oral care whitening composition may be from about 10 wt % to about 20 wt %, about 11 wt % to about 19 wt %, about 12 wt % to about 18 wt %, about 13 wt % to about 17 wt %, or about 14 wt % to about 16 wt %. In a typical implementation, the amount of the acyl donor present in the oral care whitening composition is about 15 wt %.

Enzymes Having Perhydrolytic Activity

The oral care composition of the present disclosure may include one or more enzymes having perhydrolytic activity. The one or more enzymes having perhydrolytic activity include any enzyme capable of catalyzing a reaction between the one or more sources of hydrogen peroxide or the hydrogen peroxide generated therefrom as described herein and a suitable substrate, i.e., an acyl donor of the present disclosure, to generate a whitening enhancer. Typically, the enzyme is a perhydrolyase. Perhydrolases are enzymes that generate peroxyacid via perhydrolysis. In enzyme-catalyzed perhydrolysis reactions, the acyl donor substrate (a peroxyacid precursor) is combined with a source of hydrogen peroxide and water. The perhydrolase catalyzes the formation of a peroxyacid, such as peracetic acid.

Enzymes having perhydrolytic activity include certain lipases, proteases, esterases, acyl transferases, aryl esterases, carbohydrate esterases, and combinations thereof. Examples include the perhydrolytic proteases disclosed in U.S. Pat. No. 7,510,859, which is herein incorporated by reference in its entirety, the perhydrolytic aryl esterases disclosed in U.S. Pat. No. 8,663,616, which is herein incorporated by reference in its entirety and the perhydrolytic aryl esterase/acyl transferase from *Mycobacterium smegmatis*, which is disclosed in U.S. Pat. No. 8,663,616. Typically, the perhydrolase is a perhydrolase carbohydrate esterase.

Even more typically, the perhydrolase carbohydrate esterase suitable for inclusion in the present oral care whitening compositions is a member of the carbohydrate esterase family 7 (CE-7). Enzymes from the CE-7 family are well known in the art (see Coutinho, P. M., Henrissat, B. "Carbohydrate-active enzymes: an integrated database approach" in Recent Advances in Carbohydrate Bioengineering, H. J. Gilbert, G. Davies, B. Henrissat and B. Svensson eds., (1999) The Royal Society of Chemistry, Cambridge, pp. 3-12, which is herein incorporated by reference in its entirety). The CE-7 family of enzymes has been demonstrated to be particularly effective for producing peroxyacids acids from a variety of acyl donor substrates when combined with a source of peroxygen, e.g., hydrogen peroxide (U.S. Pat. Nos. 7,794,378; 7,951,566; 7,723,083; and 7,964,378 and U.S. Patent Application Publication Nos. 2008-0176299, 2010-0087529, 2011-0081693, and 2011-0236335 to DiCosimo et al.; each incorporated herein by reference in its entirety).

Members of the CE-7 family, which include, e.g., cephalosporin C deacetylases (CAHs; E.C. 3.1.1.41) and acetyl xylan esterases (AXEs; E.C. 3.1.1.72), share a conserved signature motif (Vincent et al., *J. Mol. Biol.*, 330:593-606 (2003), which is herein incorporated by reference in its entirety). The signature motif for CE-7 family members comprises three conserved motifs as follows (residue position numbering relative to reference sequence SEQ ID NO: 2; the CE-7 perhydrolase from *B. subtilis* ATCC® 31954™).

The relative numbering accounts for small insertions or deletions (for example, typically five amino acids of less) within the aligned sequence.

The CE-7 signature motif includes: a) arginine ("Arg" or "R") at position 118, glycine ("Gly" or "G") at position 119 and glutamine ("Gln" or "Q") at position 120 of SEQ ID NO: 2; b) G at position 179, any amino acid ("XAA" or "X") at position 180, serine ("Ser" or "S") at position 181, Q at position 182 and G at position 183 of SEQ ID NO: 2; and c) histidine ("His" or "H") at position 298 and glutamic acid ("Glu" or "E") at position 299 of SEQ ID NO: 2.

Typically, the X at amino acid residue position 180 is glycine, alanine ("Ala" or "A"), proline ("Pro" or "P"), tryptophan ("Trp" or "W") or threonine ("Thr" or "T"). In some implementations, the X at amino acid residue position 180 is selected from the group consisting of glycine, alanine, proline, tryptophan, and threonine.

Further analysis of the conserved motifs within the CE-7 family indicates the presence of an additional conserved motif (Leucine ("Leu" or "L"), X and aspartic acid ("Asp" or "D"), i.e., LXD at amino acid positions 267-269 of SEQ ID NO: 2, that may be used to further define a perhydrolase belonging to the CE-7 carbohydrate esterase family. The X at amino acid residue position 268 is typically isoleucine ("Ile" or "I"), valine "Val" or "V" or methionine ("Met" or "M").

A number of well-known global alignment algorithms (i.e., sequence analysis software) may be used to align two or more amino acid sequences representing enzymes having perhydrolase activity to determine if the enzyme is comprised of the present signature motif. The aligned sequence(s) are compared to the reference sequence (SEQ ID NO: 2) to determine the existence of the signature motif.

In some implementations, a CLUSTAL alignment (such as CLUSTALW, e.g., version 1.83) using a reference amino acid sequence (as used herein the perhydrolase sequence, SEQ ID NO: 2) from the *Bacillus subtilis* ATCC® 31954™) is used to identify perhydrolases belonging to the CE-7 family. CLUSTAL is a series of widely used computer programs in bioinformatics for multiple sequence alignment and is described, for example, in Larkin et al., *Bioinformatics*, 2007 23(21): 2947-2948. doi:10.1093/bioinformatics/btm404, See also Higgins and Sharp, CABIOS, 5:151-153 (1989); Higgins et al., Nucleic Acids Res. 22:4673-4680 (1994); and Chema et al., Nucleic Acids Res 31 (13):3497-500 (2003)), which are each incorporated herein by reference in its entirety.

CLUSTAL (such as CLUSTALW, e.g., version 1.83 or CLUSTAL OMEGA e.g., version 1.2.3), is available from the European Molecular Biology Laboratory via the European Bioinformatics Institute. Suitable parameters for CLUSTALW or CLUSTAL OMEGA protein alignments include default parameters. Other suitable parameters for CLUSTAL W include GAP Existence penalty=15, GAP extension=0.2, matrix=Gonnet (e.g., Gonnet250), protein ENDGAP=−1, protein GAPDIST=4, and KTUPLE=1. In some implementations, a fast or slow alignment is used with the default settings where a slow alignment is more desirable. Alternatively, the parameters using the CLUSTALW method (e.g., version 1.83) may be modified to also use KTUPLE=1, GAP PENALTY=10, GAP extension=1, matrix=BLOSUM (e.g., BLOSUM64), WINDOW=5, and TOP DIAGONALS SAVED=5.

Examples of other suitable algorithms that may be used to identify sequences comprising the present signature motif (when compared to the reference sequence) include, but are not limited to, Needleman and Wunsch (J. Mol. Biol. 48, 443-453 (1970); a global alignment tool) and Smith-Waterman (J. Mol. Biol. 147:195-197 (1981); a local alignment tool). In some implementations, a Smith-Waterman alignment is used with default parameters. An example of suitable default parameters include the use of a BLOSUM62 scoring matrix with GAP open penalty=10 and a GAP extension penalty=0.5.

Typically, the oral care whitening compositions of the present disclosure include one or more enzymes having perhydrolytic activity that comprise a CE-7 signature motif that aligns with SEQ ID NO: 2 using, e.g., CLUSTALW, the CE-7 signature motif comprising a) an RGQ motif at positions corresponding to positions 118-120 of SEQ ID NO: 2; b) a GXSQG (SEQ ID NO: 3) motif at positions corresponding to positions 179-183 of SEQ ID NO: 2 and a HE motif at positions corresponding to positions 298-299 of SEQ ID NO:2.

In some implementations, the enzyme used in the present oral care whitening compositions is a "CE-7 variant", i.e., a CE-7 perhydrolase having a genetic modification that results in at least one amino acid addition, deletion, and/or substitution when compared to the corresponding enzyme (typically a wild type CE enzyme) from which the variant was derived; so long as the CE-7 signature motif and the associated perhydrolytic activity are retained. Examples of CE-7 variants suitable for use in the present oral care whitening compositions are provided in U.S. Pat. No. 8,663,616, which is herein incorporated by reference in its entirety. A typical variant for use in the present oral care whitening compositions is SEQ ID NO: 1, wherein a serine is substituted for the cysteine present at position 277 in wild type *Thermotoga maritima* perhydrolase.

In some implementations, the perhydrolase of the present disclosure is a CE-7 variant comprising the CE-7 signature motif and having at least 33%, more typically at least 40%, more typically at least 42%, more typically at least 50%, more typically at least 60%, more typically at least 70%, more typically at least 80%, more typically at least 90%, and yet even more typically at least 90%, 91%, 92%, 93%, 94%, 95%, 96%, 97%, 98%, or 99% amino acid identity to SEQ ID NO: 1 (EZ-1) or SEQ ID NO: 2. In some implementations, the oral care whitening compositions of the present disclosure include an enzyme comprising an amino acid sequence having at least 80% amino acid sequence identity to SEQ ID NO:1. In other implementations, the oral care whitening composition of the present disclosure includes an enzyme comprising the amino acid sequence of SEQ ID NO: 1.

As used herein the term "percent identity" refers to a relationship between two or more amino acid sequences (or polypeptide sequences, which is used interchangeably herein with the term "amino acid sequence") or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" can be readily calculated by known methods, including but not limited to those described in: Biocomputing: Informatics and Genome Projects (Smith, D. W., ed.) Academic Press, NY (1993). Methods to determine identity are codified in publicly available computer programs, such as CLUSTALW or CLUSTAL OMEGA as described herein and as well known in the art.

The skilled artisan recognizes that variants of SEQ ID NO: 1, other CE-7 variants or SEQ ID NO: 2 (retaining the signature motifs) may also be obtained by hybridization. For example, variants of, e.g., SEQ ID NO: 1 may be identified by their ability to hybridize, under highly stringent conditions with the nucleic acid molecules associated with the amino acid sequence of SEQ ID NO: 1.

As used herein, a nucleic acid molecule is "hybridizable" to another nucleic acid molecule, such as a cDNA, genomic DNA, or RNA, when a single strand of the first molecule can anneal to the other molecule under appropriate conditions of temperature and solution ionic strength. Hybridization and washing conditions are well known and exemplified in Sambrook, J. and Russell, D., T. Molecular Cloning: A Laboratory Manual, Third Edition, Cold Spring Harbor Laboratory Press, Cold Spring Harbor (2001). The conditions of temperature and ionic strength determine the "stringency" of the hybridization. Stringency conditions can be adjusted to screen for moderately similar molecules, such as homologous sequences from distantly related organisms, to highly similar molecules, such as genes that duplicate functional enzymes having perhydrolytic activity from closely related organisms.

Post-hybridization washes generally determine stringency conditions. Typically, the washing conditions include a series of washes starting with 6×SSC, 0.5% SDS at room temperature for 15 minutes, then repeated with 2×SSC, 0.5% SDS at 45° C. for 30 minutes, and then repeated twice with 0.2×SSC, 0.5% SDS at 50° C. for 30 minutes. A more typical set of conditions uses higher temperatures in which the washes are identical to those above except for the temperature of the final two 30 minute washes in 0.2×SSC, 0.5% SDS was increased to 60° C. Another typical set of highly stringent hybridization conditions includes 0.1×SSC, 0.1% SDS, 65° C. and washed with 2×SSC, 0.1% SDS followed by a final wash 10, of 0.1% SSC, 0.1% SDS, 65° C.

In some implementations, variants of, e.g., SEQ ID NO: 1 comprising the above-identified CE-7 signature motifs, may be produced by mutagenesis. Various methods are known for mutating a nucleic acid sequence to produce a nucleic acid product with altered or enhanced activity including, but not limited to 1) random mutagenesis, 2) domain swapping (using zinc finger domains or restriction enzymes, 3) error-prone PCR (Melnikov at al., Nucleic Acids Research 27(4):1056-1062 (1999)); 4) site directed mutagenesis (Coombs at al., Proteins (1998), pp 259-311); and 5) "gene shuffling" (U.S. Pat. Nos. 5,605,793; 5,811,238; 5,830,721; and 5,837,458, incorporated herein by reference). Proposed modifications are well within the routine skill in the art, as is determination of retention of biological activity of the encoded products.

In some implementations, the variants of, e.g., SEQ ID NO: 1 may demonstrate improved perhydrolysis activity in comparison to wild type enzymes or in comparison to SEQ ID NO: 1. Preparation of such variants may include, e.g., construction of an expression vector comprising the nucleotide sequence encoding a polypeptide that is structurally classified as a CE-7 enzyme or SEQ ID NO: 1, mutagenesis of the enzyme coding sequence, and finally isolation of variants with increased peroxyacid, such as peracetic acid, generation activity. Subsequent rounds of mutagenesis, if desired, allow for evolution of the enzyme-coding sequence. If desired, the regions of an enzyme important for enzymatic activity can be determined through routine site-directed mutagenesis, expression of the resulting variant polypeptides, and determination of their activities. Mutants may include deletions, insertions and point mutations, or combinations thereof.

The enzyme powder having perhydrolytic activity may have a particle size median diameter (D50) from about 100

μm to about 300 μm. For example, the particle size median diameter (D50) of the enzyme may be from about 100 μm, about 110 μm, about 120 μm, about 130 μm, about 140 μm, about 150 μm, about 160 μm, about 170 μm, about 180 μm, about 190 μm, or about 200 μm to about 210 μm, about 220 μm, about 230 μm, about 240 μm, about 250 μm, about 260 μm, about 270 μm, about 280 μm, about 290 μm, or about 300 μm. In another example, the enzyme may have a particle size median diameter (D50) from about 100 μm to about 300 μm, about 110 μm to about 290 μm, about 120 μm to about 280 μm, about 130 μm to about 270 μm, about 140 μm to about 260 μm, about 150 μm to about 250 μm, about 160 μm to about 240 μm, about 170 μm to about 230 μm, about 180 μm to about 220 μm, or about 190 μm to about 210 μm.

The enzyme having perhydrolytic activity may be provided in the form of a powder, an enzyme powder, or a stabilized enzyme powder. Methods for making and stabilizing the enzyme powder are described in U.S. Patent Application Publication Nos. 2010-0086534 and 2010-0086535, the disclosures of which are incorporated herein by reference. The enzyme may be present in the enzyme powder in an amount of about 0.5 wt % to about 75 wt %, based on a dry weight of the enzyme powder. In a typical implementation, the enzyme may be present in the enzyme powder in an amount of about 10 wt % to about 50 wt %, or more typically in an amount of about 20 wt % to about 33 wt %, based on a dry weight of the enzyme powder.

The enzyme powder may include an excipient. The excipient may be or provide the balance of the enzyme powder. Accordingly, in at least one example, the enzyme powder may include only the enzyme and the excipient. In another example, the enzyme powder may include the enzyme, the excipient, and at least one additional component. The excipient may be an oligosaccharide having a number average molecular weight of at least about 1,250 and a weight average molecular weight of at least about 9,000. The oligosaccharide excipient may have a number average molecular weight of at least about 1,700 and a weight average molecular weight of at least about 15,000. Illustrative oligosaccharides may be or include, but are not limited to, maltodextrin, xylan, mannan, fucoidan, galactomannan, chitosan, raffinose, stachyose, pectin, insulin, levan, graminan, amylopectin, sucrose, lactulose, lactose, maltose, trehalose, cellobiose, nigerotriose, maltotriose, melezitose, maltotriulose, raffinose, kestose, and the like, and cominations or mixtures thereof. The oligosaccharides may also include, but are not limited to, water-soluble non-ionic cellulose ethers, such as hydroxymethyl-cellulose and hydroxypropylmethylcellulose, and mixtures thereof. The one or more excipients may be or include, but are not limited to, trehalose, lactose, sucrose, mannitol, sorbitol, glucose, cellobiose, α-cyclodextrin, carboxymethylcellulose, and the like, and combinations thereof. In a typical implementation, the oligosaccharide excipient is maltodextrin.

Oral Care Whitening Enhancer

As discussed above, the one or more enzymes having perhydrolytic activity may be configured to catalyze a reaction between the one or more sources of hydrogen peroxide, or the hydrogen peroxide thereof, and the one or more acyl donors to generate the oral care whitening enhancer. For example, the enzyme having perhydrolytic activity may be configured to catalyze a reaction between the one or more acyl donors and the hydrogen peroxide released from the sources of hydrogen peroxide to generate the oral care whitening enhancer. In at least one implementation, the oral care whitening enhancer is peroxyacid or peracetic acid.

The amount or concentration of the peracetic acid generated by perhydrolysis may vary widely. In at least one implementation, the amount of the peracetic acid generated may be from about 0.1 ppm to about 10,000 ppm based on a total weight of an oral care product (e.g., dentifrice, whitening gel, etc.) or the oral care whitening composition thereof. For example, the amount of the peracetic acid generated may be from about 0.1 ppm, about 0.5 ppm, about 1 ppm, about 5 ppm, about 10 ppm, about 15 ppm, about 20 ppm, about 50 ppm, about 100 ppm, about 150 ppm, about 200 ppm, about 300 ppm, about 500 ppm, about 600 ppm, about 700 ppm, about 800 ppm, or about 900 ppm to about 1,000 ppm, about 1,200 ppm, about 1,400 ppm, about 1,600 ppm, about 1,800 ppm, about 2,000 ppm, about 2,500 ppm, about 3,000 ppm, about 3,500 ppm, about 4,000 ppm, about 5,000 ppm, about 6,000 ppm, about 7,000 ppm, about 8,000 ppm, about 9,000 ppm, or about 10,000 ppm. In another example, the amount of the peracetic acid generated may be less than 0.1 ppm, less than 0.5 ppm, less than 1 ppm, less than 5 ppm, less than 10 ppm, less than 15 ppm, less than 20 ppm, less than 50 ppm, less than 100 ppm, less than 150 ppm, less than 200 ppm, less than 300 ppm, less than 500 ppm, less than 600 ppm, less than 700 ppm, less than 800 ppm, less than 900 ppm, less than 1,000 ppm, less than 1,200 ppm, less than 1,400 ppm, less than 1,600 ppm, less than 1,800 ppm, less than 2,000 ppm, less than 2,500 ppm, less than 3,000 ppm, less than 3,500 ppm, less than 4,000 ppm, less than 5,000 ppm, less than 6,000 ppm, less than 7,000 ppm, less than 8,000 ppm, less than 9,000 ppm, or less than 10,000 ppm. In a typical implementation, the amount of the peracetic acid generated is less than 2000 ppm based on a total weight of the oral care product or the oral care whitening composition thereof.

In at least one implementation, the generation of the oral care whitening enhancer from the oral care composition may be initiated by contact with water. For example, contacting the oral care whitening composition with water may initiate perhydrolysis to thereby generate the whitening enhancer. In another implementation, the generation of the oral care whitening enhancer from the oral care whitening composition may be initiated by contact with a surface of the oral cavity. For example, contacting the oral care whitening composition with a surface of the oral cavity, or the saliva thereof, may initiate perhydrolysis to thereby generate the oral care whitening enhancer.

In at least one implementation, the oral care whitening enhancer of the oral care composition may be generated within at least 3 minutes (min) from contacting the oral care whitening composition with water or initiation of the perhydrolysis reaction. For example, the whitening enhancer of the oral care whitening composition may be generated in less than or equal to 3 min, less than or equal to 2.8 min, less than or equal to 2.6 min, less than or equal to 2.4 min, less than or equal to 2.2 min, less than or equal to 2.0 min, less than or equal to 1.8 min, less than or equal to 1.6 min, less than or equal to 1.4 min, less than or equal to 1.2 min, less than or equal to 1.0 min, less than or equal to 0.8 min, less than or equal to 0.6 min, or less than or equal to 0.4 min. In a typical implementation, the oral care whitening enhancer is generated within two minutes from contacting the oral care whitening composition with water.

Non-Aqueous Anhydrous Liquid or Viscosity Control Agents

In at least one implementation, the oral care composition and/or the anhydrous matrix thereof may include a non-aqueous anhydrous liquid configured to control the viscosity thereof and/or suspend a component (e.g., solid) disposed or dispersed therein. Illustrative non-aqueous anhydrous liquids or viscosity control agents may be or include, but are not limited to, polypropylene glycol, materials containing propylene oxide groups, materials containing polyethylene oxide groups, polyoxyethylene-polyoxypropylene glycols, polysorbate 20 (TWEEN™ 20), POLOXAMER™ 124 (PLURONIC™ L44), polyethylene oxide-polypropylene oxide block copolymer having the formula (EO)x(PO)y (EO)z with x=11±3, z=11±3 and y=21±5, POLOXAMER™ L35, POLOXAMER™ L31, polyethylene glycol 55 (PEG-55), glycerin, diethylene glycol, CREMOPHOR™ polyoxyethyleneglyceroltriricinoleat, GLUCAM™ P-10 propylene glycol ether of methyl glucose with 10 polypropylene oxide units, PLURIOL™ E300 alkoxylates based on ethylene oxide and propylene oxide, sodium cumene sulfonate (SCS), sodium xylene sulfonate (SXS), GLUCAM™ P-20 propylene glycol ether of methyl glucose with 20 polypropylene oxide units, GLUCAM™ E-20 ethylene glycol ether of methyl glucose with 20 polyethylene oxide units, GLUCAM™ E-10 ethylene glycol ether of methyl glucose with 10 polyethylene oxide units, and short chain ethoxylated propoxylated alcohols such as PPG2-Buteth-3, PPG3-Buteth-5, or PPG5-Buteth-7. Illustrative non-aqueous anhydrous liquids or viscosity control agents may also be or include, but are not limited to, Pluronic® L35, Pluronic® L43, Pluronic® L64, Pluronic® L10, Pluronic® L44, Pluronic® L62, Pluronic® 10R5, Pluronic® 17R4, Pluronic® L25R4, Pluronic® P84, Pluronic® P65, Pluronic® P104, Pluronic® P105, and the like, and combinations thereof, which are commercially available from BASF of Mount Olive, N.J. In a typical implementation, the non-aqueous anhydrous liquid is or includes a poly(ethylene glycol)-block-poly(propylene glycol)-block-poly(ethylene glycol) or PEG-PPG-PEG (PLURONIC® L-35).

The amount of the non-aqueous anhydrous liquid or viscosity control agents present in the oral care whitening composition and/or the anhydrous matrix thereof may vary widely. In at least one implementation, the amount of the non-aqueous anhydrous liquid or viscosity control agents present in the oral care whitening composition and/or the anhydrous matrix thereof may be from about 10 wt % to about 80 wt %, based on a total weight of an oral care product (e.g., dentifrice, whitening gel, etc.) or the oral care whitening composition thereof. For example, the amount of the non-aqueous anhydrous liquid or viscosity control agents present in the oral care whitening composition and/or the anhydrous matrix thereof may be from about 10 wt %, about 15 wt %, about 20 wt %, about 25 wt %, about 30 wt %, about 35 wt %, about 40 wt %, about 45 wt %, about 50 wt %, about 55 wt %, or about 60 wt % to about 65 wt %, about 70 wt %, about 75 wt %, or about 80 wt %. In another example, the amount of the non-aqueous anhydrous liquid or viscosity control agents present in the oral care whitening composition and/or the anhydrous matrix thereof may be from about 40 wt % to about 80 wt %, about 42 wt % to about 78 wt %, about 44 wt % to about 76 wt %, about 46 wt % to about 74 wt %, about 48 wt % to about 72 wt %, about 50 wt % to about 70 wt %, about 52 wt % to about 68 wt %, about 54 wt % to about 66 wt %, about 56 wt % to about 62 wt %, or about 58 wt % to about 62 wt %. In yet another implementation, the amount of the non-aqueous anhydrous liquid or viscosity control agents present in the oral care whitening composition and/or the anhydrous matrix thereof may be greater than or equal to 40 wt %, greater than or equal to 42 wt %, greater than or equal to 44 wt %, greater than or equal to 46 wt %, greater than or equal to 48 wt %, greater than or equal to 50 wt %, greater than or equal to 52 wt %, greater than or equal to 53 wt %, greater than or equal to 54 wt %, greater than or equal to 66 wt %, greater than or equal to 68 wt %, or greater than or equal to 70 wt %.

Thickening System

In at least one implementation, the oral care composition may include a thickening system having one or more thickeners. The one or more thickeners may be any orally acceptable thickener or thickening agent. Illustrative thickeners may be or include, but are not limited to, colloidal silica, fumed silica, a cross-linked polyvinylpyrrolidone (PVP) polymer, cross-linked polyvinylpyrrolidone (PVP), and the like, and mixtures or combinations thereof. In a typical implementation, the thickening system includes a cross-linked polyvinylpyrrolidone (PVP) polymer. In a more typical implementation, the thickening system may be or include, but is not limited to, POLYPLASDONE™ XL-10, which is commercially available from Ashland Inc. of Covington, Ky.

In at least one implementation, the oral care composition may include additional and/or optional thickeners. Illustrative additional or optional thickeners may be or include, but are not limited to, carbomers (e.g., carboxyvinyl polymers), carrageenans (e.g., Irish moss, carrageenan, iota-carrageenan, etc.), high molecular weight polyethylene glycols (e.g., CARBOWAX®, which is commercially available from The Dow Chemical Company of Midland, Mich.), cellulosic polymers, hydroxyethylcellulose, carboxymethylcellulose, and salts thereof (e.g., CMC sodium), natural gums (e.g., karaya, xanthan, gum arabic, and tragacanth), colloidal magnesium aluminum silicate, and the like, and mixtures or combinations thereof.

In at least one implementation, the thickening system may include a single thickener. For example, the thickening system may include the cross-linked polyvinylpyrrolidone (PVP) polymer. In another implementation, the thickening system may include a plurality of thickeners. For example, the thickening system may include the cross-linked PVP polymer and a silica thickener. In another example, the thickening system may include a plurality of silica thickeners.

The amount or concentration of the thickening system and/or the thickeners thereof present in the oral care whitening composition may vary widely. In at least one implementation, the amount of the thickening system and/or the thickeners thereof present in the oral care whitening system may from about 10 wt % to about 30 wt % based on the total weight of the oral care whitening composition. For example, the amount of the thickening system and/or the thickeners thereof present in the oral care whitening system may be from about 10 wt %, about 11 wt %, about 12 wt %, about 13 wt %, about 14 wt %, about 15 wt %, about 16 wt %, about 17 wt %, about 18 wt %, about 19 wt %, about 20 wt %, or about 21 wt % to about 22 wt %, about 23 wt %, about 24 wt %, about 25 wt %, about 26 wt %, about 27 wt %, about 28 wt %, about 29 wt %, or about 30 wt %. In another example, the amount of the thickening system and/or the thickeners thereof present in the oral care whitening system may from about 12 wt % to about 30 wt %, about 13 wt % to about 29 wt %, about 14 wt % to about 28 wt %, about 15 wt % to about 27 wt %, about 16 wt % to about 26 wt %, about 17 wt % to about 25 wt %, about 18 wt % to about 24 wt %, about 19 wt % to about 23 wt %, or about 20 wt % to about 22 wt %. In a typical implementation, the amount of the thickening system and/or the thickeners thereof present in the whitening system may be from about 20 wt % to about 22 wt %, more typically about 21 wt %.

Additional illustrative thickeners may be or include, but are not limited to, carbomers, also known as carboxyvinyl polymers, carrageenans, also known as Irish moss and more particularly carrageenan (iota-carrageenan), high molecular weight polyethylene glycols (such as CARBOWAX™, which is commercially available from The Dow Chemical Company), cellulosic polymers such as hydroxyethylcellulose, carboxymethylcellulose ("CMC") and salts thereof, e.g., CMC sodium, natural gums such as karaya, xanthan, gum arabic and tragacanth, colloidal magnesium aluminum silicate, and colloidal or fumed silica and mixtures of the same. The thickeners may be a combination of one or more orally acceptable thickeners.

In some implementations, the oral care product or the oral care whitening composition thereof includes from about 0.1% to about 90% of the thickeners based on a total weight of the oral care product or the oral care whitening composition thereof. In other implementations, the oral care product or the oral care whitening composition thereof includes from about 0.2% to about 50% of the thickeners. In yet another implementation, the oral care product or the oral care whitening composition thereof includes from about 0.5% to about 35% of the thickeners based on a total weight of the oral care product or the oral care whitening composition thereof. For example, the oral care product or the oral care whitening composition thereof may include about 2.3% fumed silica.

Vehicle

The oral care composition may form at least a portion of or be used in one or more oral care products. Illustrative oral care products may include, but are not limited to, a toothpaste (dentifrice), a prophylactic paste, a tooth powder, a tooth polish, a tooth gel (e.g., whitening gel), a chewing gum, a lozenge, a mouthwash, a whitening strip, a paint-on gel, varnish, veneer, and tube, syringe or dental tray comprising a gel or paste, or a gel or paste coated on an application support such as dental floss or a toothbrush (e.g., a manual, electric, sound, a combination thereof or ultrasound toothbrush). In a typical implementation, the oral care whitening composition may form at least a portion of or be used in a toothpaste. The oral care whitening composition may include or be combined with an orally acceptable vehicle to form the oral care product. In an exemplary implementation, the orally acceptable vehicle may include glycerin.

The orally acceptable vehicle may include humectants, surface active agents, gelling agents, and the like, and combinations thereof. Illustrative humectants may be or include, but are not limited to, glycerin, propylene glycol, and the like, and combinations thereof. In at least one implementation, the humectant is present in an amount of from about 20 wt % to about 60 wt % based on a total weight of the oral care product. In at least one implementation, the oral care product and/or the oral care whitening composition thereof is free or substantially free of polyol humectants. For example, the oral care product and/or the oral care whitening composition thereof does not contain any polyols as a humectant. In another implementation, the propylene glycol is present in an amount of from about 10 wt % to about 20 wt % based on a total weight of the oral care product. In another implementation, the glycerin is present in an amount of from about 25 wt % to about 40 wt % based on a total weight of the oral care product.

In at least one implementation, the components of the oral care product or the oral care whitening composition thereof may be combined with one another to provide a target viscosity. As used herein, the term "viscosity" may refer to the internal resistance to flow exhibited by a fluid (e.g., water) or the ratio of shearing stress to rate of shear, and may be measured in poise or centipoise (cP). The viscosity of the various compositions discussed and described herein may be determined using a Viscometer at a temperature of about 25° C. In at least one implementation, the viscosity or target viscosity of the oral care product or the oral care whitening composition thereof may be greater than or equal to about 10,000 cP and less than or equal to about 700,000 cP. For example, the viscosity or target viscosity of the oral care product or the oral care whitening composition thereof may be about 10,000 cP, about 15,000 cP, about 20,000 cP, about 25,000 cP, or about 30,000 cP to about 35,000 cP, about 40,000 cP, about 50,000 cP, about 75,000 cP, about 100,000 cP, about 120,000 cP, about 150,000 cP, about 175,000 cP, about 200,000 cP, about 300,000 cP, about 400,000 cP, about 500,000 cP, about 600,000 cP, or about 700,000 cP. In a typical implementation, the viscosity of the oral care product or the oral care whitening composition thereof is from about 30,000 cP to about 300,000 cP.

Additional Ingredients

The oral care product or the oral care whitening composition thereof may include additional ingredients common to oral care products. Illustrative additional ingredients may include thickeners, flavoring agents, tartar control agents, surfactants, sweeteners, humectants, colorants, dyes, and pigments. In some implementations, the oral care product or the oral care whitening composition thereof may include most orally acceptable additional ingredients common to oral care compositions. However, in some implementation, the orally acceptable additional ingredient must be selected in view of the requirement to maintain a non-aqueous or a substantially non-aqueous oral care product or oral care whitening composition. For example, in some implementations the additional ingredients will not affect the non-aqueous nature of the oral care product or the oral care whitening composition thereof.

In one implementation, the oral care product or composition, or the oral care whitening composition thereof, includes one or more surfactants. In some implementations, the surfactants enhance stability of the composition, help clean the oral cavity surfaces through detergency, and provide foam upon agitation, e.g., during brushing with an oral care product of the disclosure. Surfactants or surface active agents generally achieve increased whitening action by thoroughly dispersing the oral care whitening composition or the whitening enhancer thereof throughout the oral cavity. In various implementations, suitable surfactants or surface active agents may function as a surface active agent, emulsifier, and/or foam modulator.

Any orally acceptable surfactant, most of which are anionic, nonionic, cationic, or amphoteric, can be used. A combination of surfactants may also be used. Suitable anionic surfactants include without limitation water-soluble salts of $C_{8-20}$ alkyl sulfates, sulfonated monoglycerides of $C_{8-20}$ fatty acids, sarcosinates, taurates and the like. Illustrative examples of these and other classes include sodium lauryl sulfate, sodium cocoyl monoglyceride sulfonate, sodium lauryl sarcosinate, sodium lauryl isoethionate, sodium laureth carboxylate, and sodium dodecyl benzenesulfonate. Suitable nonionic surfactants include without limitation poloxamers, polyoxyethylene sorbitan esters, fatty alcohol ethoxylates, alkylphenol ethoxylates, tertiary amine oxides, tertiary phosphine oxides, dialkyl sulfoxides and the like. Suitable amphoteric surfactants include, without limitation, derivatives of $C_{8-20}$ aliphatic secondary and tertiary amines having an anionic group such as carboxylate, sulfate, sulfonate, phosphate or phosphonate. A suitable example is cocoamidopropyl betaine.

In some implementations, the oral care product/composition or the oral care whitening composition thereof includes from about 0.01% to about 20.0% surfactant based on a total weight of the oral care composition. In other implementations, the oral care composition includes from about 1.0% to about 10.0% surfactant. In one implementation, the oral care composition or the oral care whitening composition thereof includes about 2% surfactant based on a total weight of the oral care composition or the oral care whitening composition thereof. For example, the oral care composition or the oral care whitening composition thereof may include about 2% sodium lauryl sulfate.

In some implementations, the oral care product or the oral care whitening composition thereof includes an antioxidant. Acceptable antioxidants include BHA, BHT, vitamin A, carotenoids, vitamin E, flavonoids, polyphenols, ascorbic acid, herbal antioxidants, chlorophyll, melatonin and mixtures thereof. In some implementations, the oral care product or the oral care whitening composition thereof includes from about 0.001% to about 1% antioxidants based on a total weight of the oral care composition. In one implementation, the oral care composition includes about 0.03% antioxidant by weight.

According to one implementation, the oral care product or the oral care whitening composition thereof includes one or more flavoring agent. Useful flavoring agents include any material or mixture of materials operable to enhance the taste of the oral care composition. Any orally acceptable natural or synthetic flavoring agent can be used, such as flavoring oils, flavoring aldehydes, esters, alcohols, similar materials, and combinations thereof. Flavoring agents include vanillin, sage, marjoram, parsley oil, spearmint oil, cinnamon oil, oil of wintergreen (methylsalicylate), peppermint oil, clove oil, bay oil, anise oil, eucalyptus oil, citrus oils, fruit oils and essences including those derived from lemon, orange, lime, grapefruit, apricot, banana, grape, apple, strawberry, cherry, pineapple, etc., bean- and nut-derived flavors such as coffee, cocoa, cola, peanut, almond, etc., adsorbed and encapsulated flavorants, and mixtures thereof. Also encompassed within flavoring agents herein are ingredients that provide fragrance and/or other sensory effect in the mouth, including cooling or warming effects. Such ingredients include menthol, menthyl acetate, menthyl lactate, camphor, eucalyptus oil, eucalyptol, anethole, eugenol, cassia, oxanone, x-irisone, propenyl guaiethol, thymol, linalool, benzaldehyde, cinnamaldehyde, N-ethyl-p-menthan-3-carboxamine, N,2,3-trimethyl-2-isopropylbutanamide, 3-1-menthoxypropane-1,2-diol, cinnamaldehyde glycerol acetal (CGA), methone glycerol acetal (MGA) and mixtures thereof.

In some implementations, the oral care product or the oral care whitening composition thereof includes from about 0.01% to about 5% flavoring agents based on a total weight of the oral care composition. In another implementation, the oral care composition includes from about 0.05% to about 2% flavoring agents. In yet another implementation, the oral care composition includes from about 0.1% to about 3%, from about 0.2% to about 2.5%, or about 1.5% flavoring agents based on a total weight of the oral care composition. For example, the oral care composition may include about 1.5% of dental cream flavor.

In some implementations, the oral care product or the oral care whitening composition thereof may also include one or more sweeteners. Sweeteners among those useful herein include orally acceptable natural or artificial, nutritive or non-nutritive sweeteners. Such sweeteners include dextrose, polydextrose, sucrose, maltose, dextrin, dried invert sugar, mannose, xylose, ribose, fructose, levulose, galactose, corn syrup (including high fructose corn syrup and corn syrup solids), partially hydrolyzed starch, hydrogenated starch hydrolysate, sorbitol, mannitol, xylitol, maltitol, isomalt, aspartame, neotame, saccharin and salts thereof, sucralose, dipeptide-based intense sweeteners, cyclamates, dihydrochalcones and mixtures thereof. Some implementations may include one or more sweeteners. In some implementations, the oral care composition includes from about 0.005% to about 5% sweeteners based on a total weight of the oral care composition. In other implementations, the oral care composition includes from about 0.01% to about 1% sweeteners. For example, the oral care composition may include about 0.5% sodium saccharin and about 0.04% sucralose.

In some implementations, the oral care product or the oral care whitening composition thereof may also include one or more pH modifying agents. The pH modifying agents among those useful herein include acidifying agents to lower pH, basifying agents to raise pH and buffering agents to control pH within a desired range. For example, one or more compounds selected from acidifying, basifying and buffering agents can be included to provide a pH of 2 to 10, or in various implementations from about 2 to about 8, from about 3 to about 9, from about 4 to about 8, from about 5 to about 7, from about 6 to about 10, and from about 7 to about 9. Any orally acceptable pH modifying agent can be used, including without limitation carboxylic, phosphoric and sulfonic acids, acid salts (e.g., monosodium citrate, disodium citrate, monosodium malate, etc.), alkali metal hydroxides such as sodium hydroxide, carbonates such as sodium carbonate, bicarbonates, sesquicarbonates, borates, silicates, phosphates (e.g., monosodium phosphate, trisodium phosphate, pyrophosphate salts, etc.), imidazole and mixtures thereof. One or more pH modifying agents are optionally present in a total amount effective to maintain the composition in an orally acceptable pH range. In some implementations, the oral care composition includes from about 0.01% to about 10% pH modifier agents based on a total weight of the oral care composition. For example, the oral care composition may include about 0.9% sodium acid pyrophosphate (SAPP) and about 2% tetrasodium pyrophosphate (TSPP) as a pH modifier.

In some implementations, the oral care product or the oral care whitening composition thereof may include colorants. Colorants, such as dyes or pigments, may be food color additives presently certified under the Food Drug & Cosmetic Act for use in food and ingested drugs, including dyes such as FD&C Red No. 3 (sodium salt of tetraiodofluorescein), Food Red 17, di sodium salt of 6-hydroxy-5-{(2-methoxy-5-methyl-4-sulphophenyl)azo}-2-naphthalenesulfonic acid, Food Yellow 13, sodium salt of a mixture of the mono and disulphonic acids of quinophtalone or 2-(2-quinolyl) indanedione, FD&C Yellow No. 5 (sodium salt of 4-p-sulfophenylazo-1-p-sulfophenyl-5-hydroxypyrazole-3 carboxylic acid), FD&C Yellow No. 6 (sodium salt of p-sulfophenylazo-B-naphtol-6-monosulfonate), FD&C Green No. 3 (disodium salt of 4-{[4-(N-ethyl-p-sulfobenzylamino)-phenyl]-(4-hydroxy-2-sulfoniumphenyl)-methylene}-[1-(N-ethyl-N-p-sulfobenzyl)-DELTA-3,5-cyclohexadienimine], FD&C Blue No. 1 (disodium salt of dibenzyldiethyl-diamino-triphenylcarbinol trisulfonic acid anhydrite), FD&C Blue No. 2 (sodium salt of disulfonic acid of indigotin) and mixtures thereof in various proportions. Typically, colorants if included are present in very small quantities.

The oral care product or the oral care whitening composition thereof may also include one or more other active ingredients, which are operable for the prevention or treatment of a condition or disorder of hard or soft tissue of the oral cavity, the prevention or treatment of a physiological disorder or condition, or to provide a cosmetic benefit.

Some implementations of the present disclosure include a dental abrasive or combination of dental abrasive agents. As used herein, the term "abrasive" or "abrasive agent" also includes materials commonly referred to as "polishing agents." Any orally acceptable abrasive can be used, but typically, type, fineness (particle size) and amount of abrasive should be selected so that tooth enamel is not excessively abraded in normal use of the composition. Suitable abrasives include without limitation silica (in the form of silica gel, hydrated silica or precipitated silica), alumina, insoluble phosphates, calcium carbonate, resinous abrasives such as urea-formaldehyde condensation products and the like.

Among insoluble phosphates useful as abrasives are orthophosphates, polymetaphosphates and pyrophosphates. Illustrative examples are dicalcium orthophosphate dihydrate, calcium pyrophosphate, n-calcium pyrophosphate, tricalcium phosphate, calcium polymetaphosphate and insoluble sodium polymetaphosphate.

Average particle size of an abrasive, if present, is generally from about 0.1 to 100 about μm. For example, in one implementation, the particle size is from about 1 to about 80 μm or from about 5 to about 60 μm. In some implementations, one or more abrasives are present in an amount of from about 0.01% to about 70% by weight, based on the total weight of the oral care composition. In other implementations, the oral care composition includes from about 0.1% to about 60% abrasives. In some implementations, the abrasive is calcium pyrophosphate. In some implementations, the oral care composition includes from 0.01% to about 70% calcium pyrophosphate based on a total weight of the oral care composition. In another implementation, the oral care composition includes about 20% calcium pyrophosphate.

In various implementations of the present disclosure, the oral care product or the oral care whitening composition thereof includes an anticalculus agent. Suitable anticalculus agents include without limitation phosphates and polyphosphates (for example pyrophosphates), polyaminopropanesulfonic acid (AMPS), hexametaphosphate salts, zinc citrate trihydrate, polypeptides, polyolefin sulfonates, polyolefin phosphates, diphosphonates. In some implementations, the anticalculus agent is present in an amount of from about 0.01% to about 30% weight based on the total weight of the oral care composition. In some implementations, the oral care composition includes a mixture of anticalculus agents. In some implementations, tetrasodium pyrophosphate (TSPP) and sodium tripolyphosphate (STPP) are used as the anticalculus agents. In some implementations, the anticalculus agent includes from 0.1% to 10% TSPP, or about 2% TSPP.

Another component of the present compositions may be a synthetic anionic polymeric polycarboxylate, which acts as a stabilizer for the polyphosphate anti-tartar agent and which may help to block access of painful or pain-causing materials, such as sugars, to the tooth nerves.

In some implementations, the oral care composition optionally includes a source of fluoride ions. In some implementations, the source of fluoride ions is selected from: fluoride, monofluorophosphate (MFP), and fluorosilicate salts. In some implementations, one or more fluoride ion-releasing compounds are optionally present in an amount providing a total of 100 to 20,000 ppm, 200 to 5,000 ppm, or 500 to 2,500 ppm, fluoride ions. If present, in some implementations, the amount of fluoride source in the oral care composition ranges from about 0.01% to about 10% by weight, based on the total weight of the oral care composition, typically about 1.1%. For example, in one implementation, the oral care composition may include about 0.76% MFP.

The oral care product or the oral care whitening composition thereof also may include a stannous ion or a stannous ion source to mitigate calcium loss. Suitable stannous ion sources include without limitation stannous fluoride, other stannous halides such as stannous chloride dihydrate, stannous pyrophosphate, organic stannous carboxylate salts such as stannous formate, acetate, gluconate, lactate, tartrate, oxalate, malonate and citrate, stannous ethylene glyoxide and the like. In some implementations, one or more stannous ion sources are included in the oral care composition. For example, the oral care composition may include from about 0.01% to about 10% stannous ion source by weight, based on the total weight of the oral care composition. In one implementation, the oral care composition includes from about 0.1% to about 7% stannous ion source or from about 0.2% to about 5% stannous ion source.

All ingredients for use in the compositions described herein should be orally acceptable. As used herein, "orally acceptable" may refer any ingredient that is present in a composition as described in an amount and form which does not render the composition unsafe for use in the oral cavity.

Methods

In one or more implementations, the present disclosure may provide methods for whitening teeth in a human or animal subject with an oral care product and/or the oral care whitening composition thereof. As used herein "animal subject" may include higher order non-human mammals such as canines, felines, and horses. The method may include contacting the oral care product or the oral care whitening composition thereof with water. For example, the method may include contacting the source of hydrogen peroxide of the oral care whitening composition with water to initiate the formation of hydrogen peroxide. The method may also include generating the whitening enhancer (e.g., peracetic acid) within less than 2 min, less than 1.5 min, or less than 1 min. The method may also include contacting the surface of the teeth with the oral care whitening composition and/or the whitening enhancer generated from the enzyme-catalyzed perhydrolysis of the source of hydrogen peroxide and the acyl donor. Contacting the surface of the teeth with the oral care whitening composition may include brushing the teeth with the oral care whitening composition. Contacting the surface of the teeth with the oral care whitening composition may also include disposing the oral care whitening composition in a dental tray (e.g., reservoir of the dental tray) and disposing the dental tray about the teeth. The dental tray may be applied to the teeth and left for at least 5 minutes, typically at least 10 minutes, or more typically at least 30 minutes. After each treatment with the tooth oral care whitening composition the teeth may be treated with a tooth desensitizing formulation. Illustrative desensitizing formulations may contain potassium nitrate, citric acid, citric acid salts, strontium chloride and the like.

In at least one implementation, the oral care product and/or the oral care whitening composition thereof may be applied and/or contacted with the surfaces of the teeth at predetermined intervals. For example, a daily basis, at least once a day for multiple days, or alternatively every other day. In another example, the oral care product and/or the oral care whitening composition thereof may be applied and/or contacted with the surfaces of the teeth at least once a day, at least once every two days, at least once every three days, at least once every five days, at least once a week, at least once every two weeks, or at least once a month. The oral care product and/or the oral care whitening composition thereof may be utilized for up to 2 weeks, up to 3 weeks, up to 4 weeks, up to 6 weeks, up to 8 weeks, or greater.

The dental tray may be of any conventional form, and may be formed from conventionally used polymers, such as thermoplastic polymers. Thermoset polymers also may be used. Accordingly, the dental tray may range from highly flexible to a low flexibility. The thermoplastic polymers are typical, and those that may be used include, but are not limited to, polyethylene and polypropylene polymers, their derivatives and copolymers, silicone elastomers, polyurethanes and derivatives, polycaprolactams, polystyrene and derivatives, polybutadiene and derivatives, polyisoprene and derivatives, and polymethacrylate and its derivatives, and the like, and combinations thereof.

In at least one implementation, the present disclosure may provide a method for increasing the stability of one or more enzymes in a oral care whitening composition and/or the anhydrous matrix thereof. For example, the present disclosure may provide a method for maintaining the viability of the enzyme for an extended period of time under accelerated aging conditions. The method may include combining, mixing, suspending, or otherwise contacting the enzyme with the anhydrous matrix to form the oral care whitening composition. The oral care whitening composition, including the enzyme and the anhydrous matrix may be combined with one another in a single, homogenous phase.

The present disclosure may also provide a method for the in situ generation of peracetic acid. The method may include admixing, stirring, or otherwise contacting the oral care whitening composition including the anhydrous matrix and the enzyme having perhydrolytic activity with water (e.g., added water and/or water of the oral cavity). The method may also include contacting the source of hydrogen peroxide with water to initiate the formation of hydrogen peroxide.

EXAMPLES

The examples and other implementations described herein are exemplary and not intended to be limiting in describing the full scope of compositions and methods of this disclosure. Equivalent changes, modifications and variations of specific implementations, materials, compositions and methods may be made within the scope of the present disclosure, with substantially similar results.

Example 1

The stability of four oral care whitening compositions (1)-(4) were evaluated under accelerated aging conditions. The oral care whitening compositions (1)-(4) were prepared by combining a source of hydrogen peroxide, i.e., PVP-Peroxide (PEROXYDONE™ XL 10), an acyl donor, i.e., Triacetin (TA), a perhydrolase enzyme, a thickener or cross-linked polyvinylpyrrolidone (PVP), i.e., POLYPLASDONE™ XL-10, and a non-aqueous anhydrous liquid, i.e., PLURONIC® L35, in varying amounts or concentrations. Particularly, the oral care whitening compositions (1)-(4) were prepared by combining each of the aforementioned components according to Table 1.

TABLE 1

Oral care whitening compositions (1)-(4)

| Ingredient | Composition | | | |
|---|---|---|---|---|
| | 1 | 2 | 3 | 4 |
| PVP-Peroxide (PEROXYDONE™ XL 10) (18% HP) (wt %)[A] | 0.560 | 0.560 | 0.560 | 0.560 |
| Triacetin (TA) (wt %) | 15 | 15 | 15 | 15 |
| Enzyme Suspension (wt %)[B] | 0.57 | 0.57 | 1.14 | 1.14 |
| POLYPLASDONE™ XL-10 (wt %) | 15 | 30 | 15 | 30 |
| PLURONIC® L35 (wt %) | 68.87 | 53.87 | 68.30 | 53.30 |

[A]0.560 wt % of PVP-HP contains 0.1 wt % hydrogen peroxide in the final composition.
[B]0.57 wt % of the Enzyme Suspension contains 0.1 wt % of the Enzyme in the final composition, and 1.14 wt % of the Enzyme Suspension contains 0.2 wt % of the Enzyme in the final composition.

The oral care whitening compositions (1)-(4) were then exposed to accelerated aging conditions. Particularly, each of the oral care whitening compositions (1)-(4) were aged in an incubator maintained at 40° C. and 75% Relative Humidity (RH) for 13 weeks.

The stability of each of the oral care whitening compositions (1)-(4) was evaluated by determining the amount of hydrogen peroxide (HP) contained in each of the oral care whitening compositions (1)-(4) before and after exposure to accelerated aging conditions for 13 weeks. The amount of HP contained in each of the oral care whitening compositions (1)-(4) was determined via active titration (i.e., Iodometric Titration). Particularly, about 1.3 g of each oral care whitening composition (1)-(4) was measured in respective beakers. 25 ml of glacial acetic acid was then added to each of the beakers, followed by 50 ml of an ethanol/water (1:1 v/v) solution. The resulting solution was stirred or agitated until a paste/gel was fully suspended from the mixture. Then, 5 ml of a 20 wt % potassium iodide solution and four drops of an ammonium molybdate solution/catalyst were added, and the resulting mixture was mixed for 5 minutes (min), resulting in a yellow or yellow tinted solution. 2 ml of a starch indicator was then added to each of the yellow solutions, thereby turning the yellow solution brown in color. The brown solution/mixture was then titrated with a 0.1 N sodium thiosulfate solution until the brown color dissipated, leaving a clear solution. The amount (ml) of the sodium thiosulfate solution used was then recorded and used to determine the amount of HP (wt %) in each of the oral care whitening compositions (1)-(4). The results of the active titration are summarized in Table 2.

TABLE 2

Amount of HP in Oral care whitening compositions (1)-(4) Before and After 13 weeks of Accelerated Aging Conditions

| Time | Composition | | | |
|---|---|---|---|---|
| | 1 | 2 | 3 | 4 |
| Initial (Time = 0 wks) | 0.12 | 0.12 | 0.12 | 0.12 |
| Final (Time = 13 wks) | 0.10 | 0.10 | 0.08 | 0.10 |
| Hydrogen Peroxide Loss (%) | 16.7 | 16.7 | 33.3 | 16.7 |

As illustrated in Table 2, after exposure to accelerated aging conditions, oral care whitening compositions (1), (2), and (4) exhibited increased stability relative to oral care whitening compositions (3). Particularly, oral care whitening compositions (1), (2), and (4) showed a 16.7% loss of HP (0.02 wt % loss) as compared to oral care whitening composition (3), which exhibited a 33.3% loss of HP (0.04 wt % loss). One having ordinary skill in the art, however, should appreciate that the loss of HP is not significant when taking experimental error into consideration. Generally, the results summarized in Table 2 illustrate that HP is stable and compatible with Triacetin when the perhydrolase enzyme is combined with the cross-linked PVP/block co-polymer non-aqueous anhydrous liquid base or gel matrix.

Example 2

The amount and speed of a whitening enhancer, i.e., peracetic acid (PAA), being generated from each of the oral care whitening compositions (1)-(4) of Example 1 was evaluated. The generation of PAA generated from each of the oral care whitening compositions (1)-(4) was evaluated via HPLC and UV/Vis. Since PAA is not visible via UV-Vis, secondary compounds that are visible or absorb in the UV-Vis spectrum were derived from the generated PAA via successive oxidation reactions. To derive the secondary compounds, about 0.5 g of each of the oral care whitening compositions (1)-(4) was mixed with 0.5 g of a phosphate buffer solution (pH=7.0) for two minutes. 360 µl of the resulting solution/mixture were then transferred to a microfuge tube containing 40 µl of 1.3 M phosphoric acid and mixed or agitated to reach a final pH of less than 3, thereby terminating the enzymatic reaction. 100 µl of clarified supernatant was then transferred to an HPLC container/vial containing 300 µl of water and 100 µl of a methyl tolyl sulfide (MTS) reagent, and mixed or agitated in the dark for at least 10 min, thereby reacting the PAA with the MTS reagent to produce methyl tolyl sulfoxide (MTSO) and acetic acid (AcOH). Then 400 µl of acetonitrile and 100 µl of a triphenyl phosphine (TPP) reagent was added to the solution and allowed to react in the dark for 30 min. After 30 min, 100 µl of acetonitrile was added and mixed thoroughly, and the resulting solution was analyzed via HPLC. The calculated concentration of MTSO was then corrected for dilution (i.e., during the acid quench step), concentration (i.e., during the centrifugation step), and total reaction volume. It should be appreciated that the concentration of PAA is equivalent to the calculated concentration of MTSO including the aforementioned corrections. The amount and speed of PAA generated from each of the oral care whitening compositions (1)-(4) is summarized in Table 3.

TABLE 3

Speed and Amount of PAA Generated from Oral care whitening compositions (1)-(4)

| | Composition | | | |
|---|---|---|---|---|
| | 1 | 2 | 3 | 4 |
| Time Until PAA was Sensed via Smell (sec) | 40 | 30 | 35 | 20 |
| Amount of PAA Generated (ppm) | 671 | 728 | 637 | 852 |

As illustrated in Table 3, PAA was successfully generated in situ after a matter of seconds. The generation of the PAA in situ indicates and validates that the perhydrolase enzyme was still active after exposure to accelerated aging conditions. Table 3 also illustrates the fast generation of PAA in situ; particularly, within the two minute time period for standard brushing of teeth. For example, the 671 ppm, 728 ppm, 637 ppm, and 852 ppm of PAA was generated in each of the respective oral care whitening compositions (1)-(4) after two minutes of mixing. It should be appreciated that about 500 ppm of PAA may be generally equivalent to conventional oral care products (e.g., dentifrices) containing 1% HP. For example, the performance of 500 ppm of PAA is generally equivalent to a toothpaste or other oral care product containing 1% HP. Accordingly, it should be appreciated that oral care products incorporating or including the combination of 0.1 wt % HP and 0.1% perhydrolase enzyme may exhibit relatively improved whitening efficacy as compared to oral care products including 1% HP.

The present disclosure has been described with reference to exemplary implementations. Although a limited number of implementations have been shown and described, it will be appreciated by those skilled in the art that changes may be made in these implementations without departing from the principles and spirit of the preceding detailed description. It is intended that the present disclosure be construed as including all such modifications and alterations insofar as they come within the scope of the appended claims or the equivalents thereof.

What is claimed is:

1. A single-phase oral care composition, comprising:
   a perhydrolase enzyme that catalyzes the generation of peracetic acid between a source of hydrogen peroxide and an acyl donor; and
   an anhydrous matrix comprising:
     a source of hydrogen peroxide;
     an acyl donor; and
     a polyethylene oxide-polypropylene oxide block copolymer;
   wherein the oral care composition is a single phase composition.

2. The oral care composition of claim 1, wherein the source of hydrogen peroxide is a hydrogen peroxide complex comprising a cross-linked polyvinylpyrrolidone (PVP) hydrogen peroxide complex.

3. The oral care composition according to claim 2, wherein the cross-linked polyvinylpyrrolidone (PVP) hydrogen peroxide complex is present in an amount of from about 0.1 wt. % to about 1 wt. %, of the oral care composition.

4. The oral care composition according to claim 1, wherein the source of hydrogen peroxide is present in an amount necessary to provide from about 0.05 wt. % to about 2 wt. %, of hydrogen peroxide.

5. The oral care composition according to claim 1, wherein the perhydrolase enzyme is provided in the form of a powder or a suspension.

6. The oral care composition according to claim 1, wherein the composition provides greater than 500 ppm of peracetic acid during brushing.

7. The oral care composition according to claim 1, wherein the composition provides greater than 500 ppm of peracetic acid within 2 minutes of contacting the oral cavity.

8. The oral care composition according to claim 1, wherein the perhydrolase enzyme and the hydrogen peroxide are present in a weight ratio of from about 2:1 to about 1:2.

9. The oral care composition according to claim 1, wherein the perhydrolase enzyme and the hydrogen peroxide are present in a weight ratio of about 1:1.

10. The oral care composition according to claim 1, wherein the composition is substantially free from encapsulations and film-type materials.

11. The oral care composition according to claim 1, wherein the composition is in a form selected from: a paste and a gel.

12. The oral care composition according to claim 4, wherein the oral care composition is substantially free of water.

13. The oral care composition according to claim 4, wherein the acyl donor is selected from one or more of a C2-18 carboxylic acid, a hydrolysable ester, and mixtures thereof.

14. The oral care composition according to claim 13, wherein the acyl donor comprises triacetin.

15. The oral care composition according to claim 1, further comprising a thickening system.

16. The oral care composition according to claim 15, wherein the thickening system comprises a thickener selected from: a cross-linked polyvinylpyrrolidone; silica; a carbomer; a cellulosic polymer; a natural gum; colloidal magnesium aluminum silicate; and a combination of two or more thereof.

17. The oral care composition according to claim 1, further comprising a colorant.

18. The oral care composition according to claim 17, wherein the colorant is selected from a blue dye; a blue pigment; and a combination thereof.

19. A method for whitening teeth, comprising contacting a surface of the oral cavity with the oral care composition according to claim 9.

* * * * *